(12) United States Patent
Capozzoli (10) Patent No.: US 8,845,690 B2
(45) Date of Patent: Sep. 30, 2014

(54) VARIABLE TENSION SPINE FIXATION ROD

(75) Inventor: Joseph Capozzoli, Mount Laurel, NJ (US)

(73) Assignee: DePuy Synthes Products, LLC, Raynham, MA (US)

( * ) Notice: Subject to any disclaimer, the term of this patent is extended or adjusted under 35 U.S.C. 154(b) by 590 days.

(21) Appl. No.: 12/644,708

(22) Filed: Dec. 22, 2009

(65) Prior Publication Data

US 2010/0160967 A1   Jun. 24, 2010

Related U.S. Application Data

(60) Provisional application No. 61/140,021, filed on Dec. 22, 2008.

(51) Int. Cl.
*A61B 17/70* (2006.01)
*A61B 17/88* (2006.01)

(52) U.S. Cl.
CPC ......... *A61B 17/7011* (2013.01); *A61B 17/7029* (2013.01); *A61B 17/8869* (2013.01)
USPC .......................................... 606/258; 606/254

(58) Field of Classification Search
CPC ........... A61B 17/7001; A61B 17/7002; A61B 17/7004; A61B 17/7005; A61B 17/7007; A61B 17/7008; A61B 17/701; A61B 17/7011; A61B 17/7013; A61B 17/7014; A61B 17/7019; A61B 17/702; A61B 17/7022; A61B 17/7023; A61B 17/7025; A61B 17/7026; A61B 17/7031; A61B 17/7032; A61B 17/7034; A61B 17/7035; A61B 17/7037; A61B 17/7038; A61B 17/7041; A61B 17/7043; A61B 17/7046; A61B 17/7049; A61B 17/705
USPC .................................... 606/53, 60, 246–279
See application file for complete search history.

(56) References Cited

U.S. PATENT DOCUMENTS

| | | | | |
|---|---|---|---|---|
| 3,623,164 | A | * | 11/1971 | Bokros ............................ 606/60 |
| 5,938,662 | A | * | 8/1999 | Rinner ............................ 606/60 |
| 6,290,700 | B1 | | 9/2001 | Schmotzer |
| 7,621,912 | B2 | * | 11/2009 | Harms et al. .................... 606/59 |
| 7,621,940 | B2 | * | 11/2009 | Harms et al. .................. 606/257 |

(Continued)

FOREIGN PATENT DOCUMENTS

| | | | |
|---|---|---|---|
| FR | 2 715 825 | A1 | 8/1995 |
| WO | WO 2006/136937 | A2 | 12/2006 |
| WO | WO 2007/109470 | A2 | 9/2007 |
| WO | WO 2010/075400 | | 7/2010 |

OTHER PUBLICATIONS

International Patent Application No. PCT/US09/69227: International Search Report dated Apr. 6, 2010, 7 pages.

(Continued)

*Primary Examiner* — Pedro Philogene
*Assistant Examiner* — Lynnsy Summitt
(74) *Attorney, Agent, or Firm* — Baker & Hostetler LLP (57) ABSTRACT

A variable stiffness rod is provided for use in spine stabilization systems. The variable stiffness rod system includes an outer member having a cannulation that retains a flexible tensioning inner member that can be used to adjust the stiffness of the rod via an adjustable end cap assembly that couples the inner member to the outer member at least at one end of the fixation rod.

21 Claims, 10 Drawing Sheets

(56) References Cited

U.S. PATENT DOCUMENTS

| | | | |
|---|---|---|---|
| 7,785,325 B1* | 8/2010 | Milbank | 606/62 |
| 7,799,053 B2* | 9/2010 | Haid et al. | 606/246 |
| 7,815,665 B2* | 10/2010 | Jahng et al. | 606/263 |
| 7,988,710 B2* | 8/2011 | Jahng et al. | 606/254 |
| 2005/0085815 A1* | 4/2005 | Harms et al. | 606/61 |
| 2005/0277934 A1* | 12/2005 | Vardiman | 606/61 |
| 2006/0195090 A1 | 8/2006 | Suddaby | |
| 2007/0288011 A1* | 12/2007 | Logan | 606/61 |
| 2008/0077136 A1 | 3/2008 | Triplett et al. | |
| 2008/0125777 A1* | 5/2008 | Veldman et al. | 606/61 |
| 2009/0054932 A1* | 2/2009 | Butler et al. | 606/255 |
| 2009/0099599 A1* | 4/2009 | Biedermann et al. | 606/246 |
| 2009/0131981 A1* | 5/2009 | White | 606/246 |
| 2009/0259257 A1* | 10/2009 | Prevost | 606/255 |
| 2009/0275983 A1* | 11/2009 | Veldman et al. | 606/258 |
| 2010/0042156 A1* | 2/2010 | Harms et al. | 606/254 |

OTHER PUBLICATIONS

International Patent Application No. PCT/US09/69227: International Written Opinion of the International Searching Authority, dated Apr. 6, 2010, 6 pages.

U.S. Appl. No. 61/140,021, filed Dec. 22, 2008, Synthes USA, LLC.

International Patent Application No. PCT/US09/69227: International Preliminary Exam Report dated Jan. 21, 2011, 11 pages.

* cited by examiner

FIG. 5

VARIABLE TENSION SPINE FIXATION ROD

CROSS-REFERENCE TO RELATED APPLICATIONS

This application claims priority to U.S. Provisional Patent Application No. 61/140,021, filed Dec. 22, 2008, the disclosure of which is hereby incorporated by reference as if set forth in its entirety herein.

BACKGROUND

Spinal fusion involves joining two or more adjacent vertebrae with a bone fixation device to restrict movement of the vertebrae with respect to one another. For a number of known reasons, spinal fixation devices are used in spine surgery to align and/or fix a desired relationship between adjacent vertebral bodies. Such devices typically include a spinal fixation element, such as a relatively stiff fixation rod that is coupled to adjacent vertebrae by attaching the fixation element to various bone fixation elements, such as hooks, bolts, wires, screws, and the like. The fixation elements can have a predetermined contour and, once installed, the fixation elements hold the vertebrae in a desired spatial relationship, either until desired healing or spinal fusion has taken place, or for some longer period of time.

Recently, dynamic or flexible fixation elements have come into use. Dynamic fixation elements are desirable to permit some movement and shock absorption upon implantation on a patient's spine. In addition, the removal of bone structure, such as facet joints or laminae, result in instabilities of the motion segments of the spine. Consequently, a fixation system should stabilize the motion segment in anteroposterior translation as well as in axial rotation. Both motion patterns result in shear stress within the rods of fixation systems. This is especially important in elderly patients, where the bone quality is sometimes compromised, becoming sclerotic or osteoporotic.

Excessive stiffness of a rod element may cause abnormalities and diseases of the spine, as well as significant discomfort to the patient. Although some existing spinal fixation devices do provide some level of flexibility, what is needed is a dynamic stabilization system that enables a range of flexibilities and stiffnesses to be applied to a patient's spine.

SUMMARY

In accordance with one embodiment, a variable stiffness rod is configured to span between two or more adjacent vertebral fixation elements, each vertebral fixation element including a channel formed therein configured to receive the variable stiffness rod. The variable stiffness rod includes an outer member, and inner member, and an adjustable end cap assembly. The outer member has a first end and an opposing second end, and defines an interior cannulation extending between the first and second ends. The inner tensioning member is configured to be disposed in the cannulation of the outer member. The inner tensioning member has a first stiffness. The adjustable end cap assembly is disposed at least at one of the first and second ends. The adjustable end cap assembly is configured to couple the inner tensioning member to the outer member. The adjustable end cap assembly including a translator coupled to the inner tensioning member, and an actuator configured to move in a first direction that drives the translator to extend the inner tensioning member, such that the inner tensioning member achieves a second stiffness that is greater than the first stiffness.

BRIEF DESCRIPTION OF THE DRAWINGS

The foregoing summary, as well as the following detailed description of the preferred embodiment of the present application, will be better understood when read in conjunction with the appended drawings. For the purposes of illustrating the variable tension rod of the present application, there is shown in the drawings a preferred embodiment. It should be understood, however, that the application is not limited to the precise arrangements and instrumentalities shown. In the drawings.

DETAILED DESCRIPTION

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the variable stiffness rod assembly and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Figure 1A:
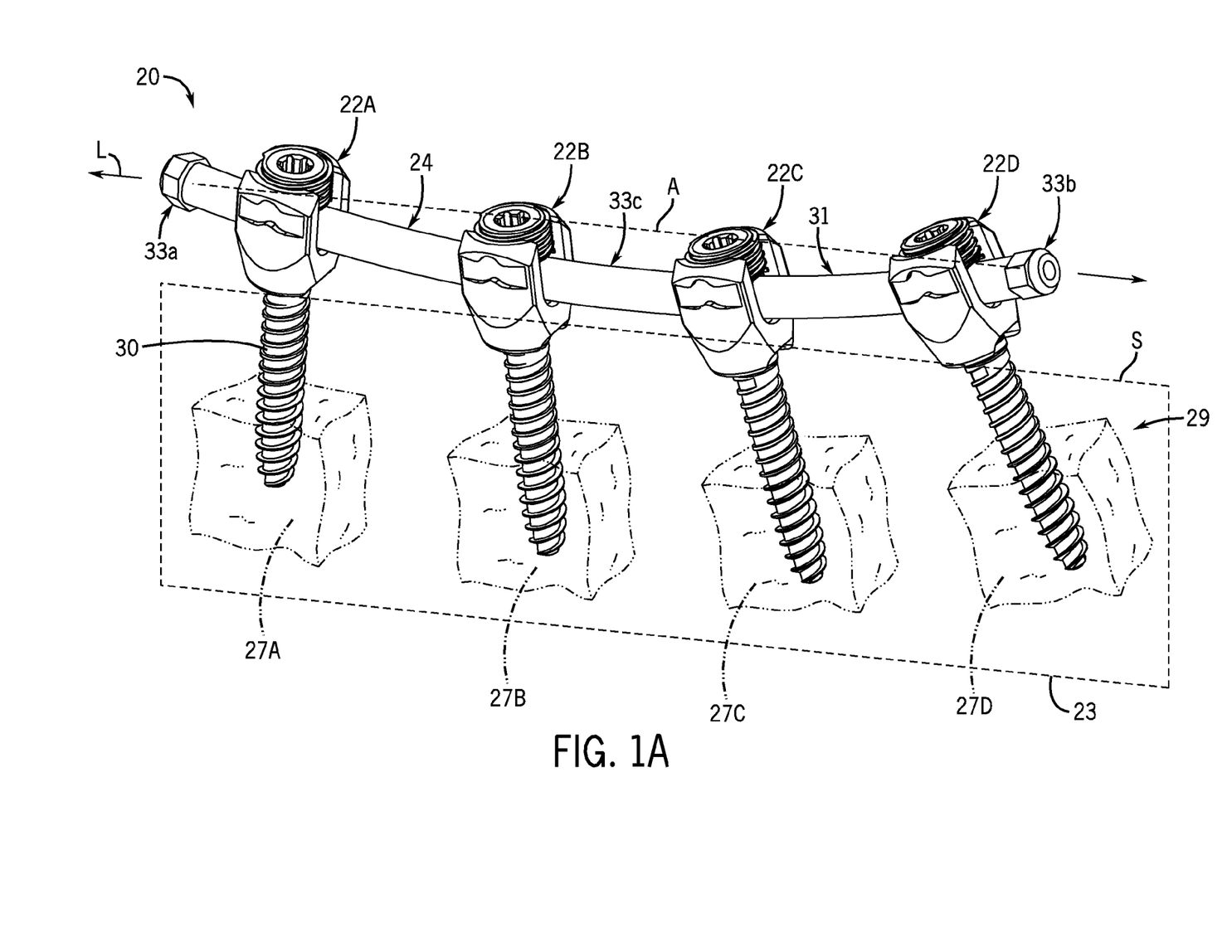
FIG. 1A is a schematic side elevation view of a bone fixation system constructed in accordance with one embodiment as including a plurality of bone fixation elements attached to underlying bone and connected to each other via a variable stiffness spine fixation rod.

Referring to FIG. 1A, a bone fixation assembly 20 includes a plurality of bone fixation elements, such as bone fixation elements 22A-D, connected by a spine fixation rod 24 that spans between the fixation elements 24A-D. As will be described in more detail below, the fixation rod 24 is configured as a variable stiffness spine fixation rod whose stiffness, or flexibility, is adjustable depending, for instance, on the desired flexibility or stiffness that is to be imparted onto the underlying vertebral bodies 27A-D. Unless otherwise specified, the bone fixation assembly 20 and its components can be made from any suitable biocompatible material such as titanium, titanium alloys such as titanium-aluminum-niobium alloy (TAN), implant-grade 316L stainless steel, poly-ether-ether-ketone (PEEK) or any suitable alternative implant-grade material.

The bone fixation elements 22A-D each include a bone anchor 30 that is implanted into a corresponding vertebra 27A-D disposed in a spinal region 29. The spinal region 29 is illustrated as the lumbar region, but can alternatively include the thoracic region or the cervical region as desired. While the fixation rod 24 is illustrated as having a length sufficient to join four bone fixation elements 22A-D, it should be appreciated that the fixation rod 24 can have any length suitable for attachment to any desired number of bone fixation elements configured to attach to any corresponding number of underlying vertebral bodies. It is recognized that the degree of spine degradation can dictate the desired level of stiffness of the fixation rod 24. For example, instances of advanced vertebral or intervertebral degradation can indicate a high degree of desired fixation rod stiffness, while initial to intermediate stages of vertebral or intervertebral degradation can indicate lower levels of desired fixation rod stiffness so as to permit greater amounts of vertebral movement.

The fixation rod 24 defines a curved profile 31 defined at least in part by a pair of opposing terminal ends 33a and 33b, and a middle portion 33c disposed between the terminal ends 33a-b and offset with respect to an imaginary straight line A that joins the terminal ends 33a-b. In the illustrated embodiment, the middle portion 33c is disposed posterior with respect to the terminal ends 33a-b when the bone fixation elements 22A-D are implanted into the spine, such that the rod 24 is convex with respect to the spinal column 23, though it should be appreciated that the fixation rod 24 could be curved when implanted such that the middle portion 33c is disposed anteriorly with respect to the terminal ends 33a-b, such that the fixation rod 24 is convex with respect to the spinal column 23. Accordingly, in the illustrated embodiment, the fixation rod 24 is curved such that the rod 24, including the terminal ends 33a-b and the middle portion 33c, lies in a desired plane, such as the sagittal plane S, when the bone fixation assembly 20 is secured to the underlying vertebrae 27A-D. In this regard, the fixation rod 24 is configured to impart a lordotic profile onto the underlying vertebrae 27A-D.

It should be appreciated that even though the fixation rod 24 is curved as illustrated, the rod is described herein as extending generally along a longitudinal direction L. Accordingly, various structure associated with the fixation rod 24 is described herein with reference to longitudinally inner and longitudinally outer directions, and derivatives thereof. The longitudinally inner direction refers to a direction from a respective one of the terminal ends 33a-b toward the middle portion 33c, while the longitudinally outer direction refers to a direction from the middle portion 33c toward a respective one of the terminal ends 33a-b. In this regard, it should be appreciated that the fixation rod 24 could be constructed as extending straight, for instance in the longitudinal direction L, if desired.

With continuing reference to FIG. 1A, the bone fixation elements 22A-D will be described as and may be generally implanted in the spine, for instance at the pedicle portion of a lumbar, thoracic, or cervical vertebral body. In this regard, when the bone fixation elements 22A-D are joined by the rod 24, the assembly 20 fixes the relative position of the vertebrae (illustrated schematically at 27A-D). Accordingly, the bone fixation elements 22A-D can be referred to as vertebral fixation elements or pedicle screw assemblies, the fixation rod 24 can be referred to as a spinal rod, and the bone fixation assembly 20 can be referred to as a spine fixation assembly.

Figure 1B:
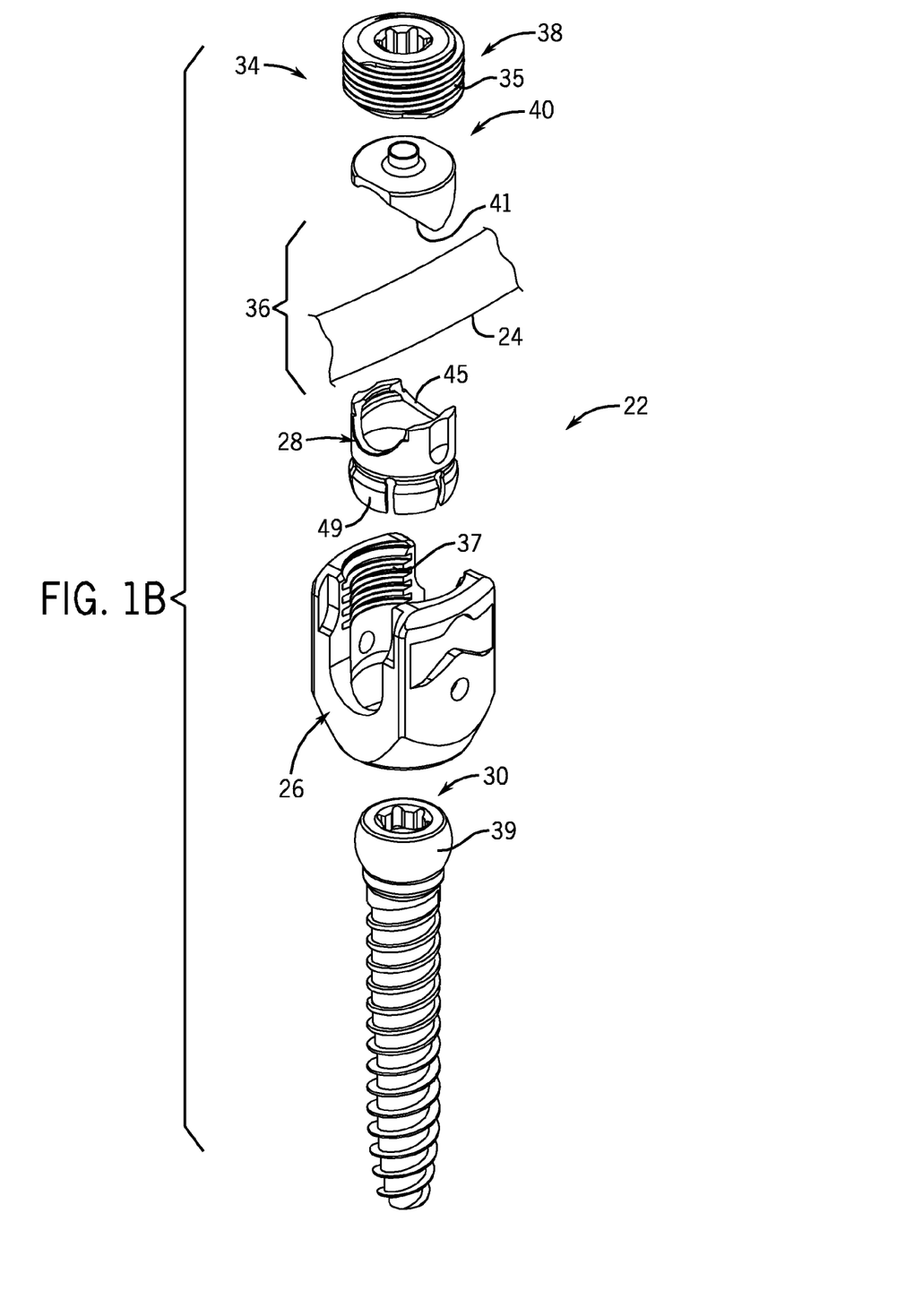
FIG. 1B is an exploded perspective view of one of the bone fixation elements illustrated in FIG. 1A.

Referring now to FIG. 1B, the bone fixation elements 22A-D of the bone fixation assembly 20 will now be described with respect to the bone fixation element 22 as illustrated. In particular, the bone fixation element 22 generally includes a bone anchor seat 26, a collet 28 disposed inside the anchor seat 26, a bone anchor 30 having a head portion 39 attached inside lower fingers 49 of the collet 28, and a locking cap 34 installed in the anchor seat 26 at a location above the collet 28.

The locking cap 34 includes a set screw 38 and a saddle 40 rotatably coupled to the set screw 38. The set screw 38 defines a threaded outer surface 35 that mates with a threaded inner surface 37 of the bone anchor seat 26. The saddle 40 defines a lower surface 41 curved to match that cross-sectional profile of the fixation rod 24. Likewise, the collet 28 defines an upper surface 45 curved to match the cross-sectional profile of the fixation rod. Thus, a rod receiving channel 36 is disposed, and as illustrated defined, between the collet 28 and the locking cap 34. The rod receiving channel 36 is configured to receive the fixation rod 24 therein.

The locking cap 34 can be actuated, such as rotated or screwed, between an unlocked position and a locked position. When the locking cap 34 is in the unlocked position, the fixation rod 24 can slide with respect to the bone fixation elements 22A-D, the bone anchor 30 is free to pivot with respect to the anchor seat 26 as desired, and the bone anchor 30 can further freely rotate relative to the anchor seat 26. When the locking cap 34 is in the locked position, such that the surfaces 41 and 45 bear tightly against the rod 24, the rod 24 is unable to move inside the channel 36, and the collet 28 becomes tightened against the bone anchor such that the bone anchor is unable to pivot or rotate with respect to the collet 28 or the anchor seat 26.

While the fixation assembly 20 has been illustrated in accordance with one embodiment, it should be appreciated that the fixation rod 24 could alternatively extend and connect between fixation elements of any alternatively constructed fixation assembly 20 that is configured to attach or span between to two or more (i.e., a plurality of) underlying vertebral bodies. For instance, while the bone fixation element 22 is illustrated in accordance with one embodiment, the bone fixation element could be described in accordance any alternative embodiment so that it is capable of attaching to the bone fixation rod 24. In this regard, while the bone anchor 30 is illustrated as a bone screw, or pedicle screw, the bone anchor can alternative be provided as a nail, pin, rivet, hook, or any alternatively constructed structure configured to be affixed to the underlying vertebrae.

Figures 2, 3A:
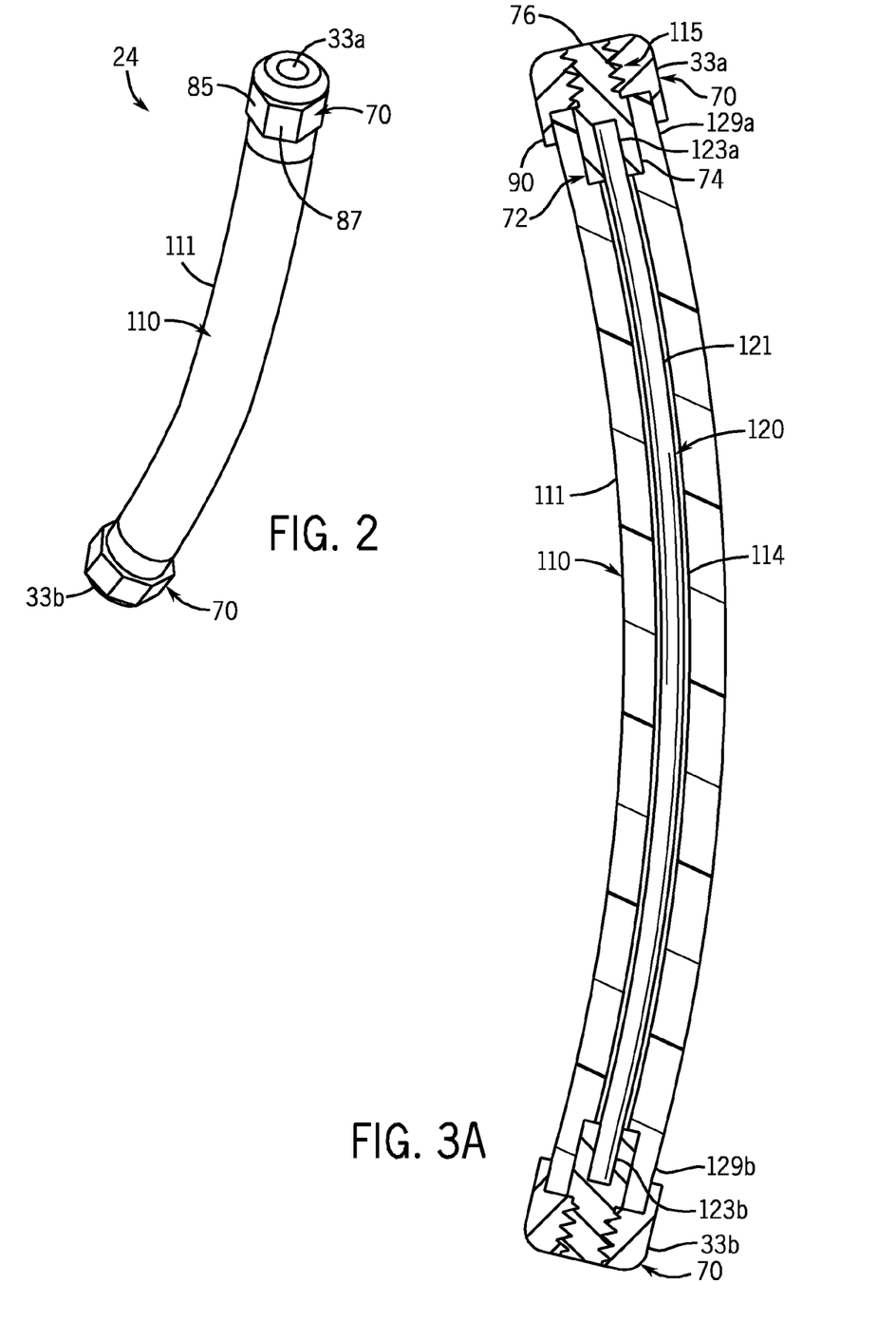
FIG. 2 is a perspective view of the variable stiffness fixation rod illustrated in FIG. 1A.
FIG. 3A is a sectional side elevation view of the variable stiffness fixation rod illustrated in FIG. 2, including an outer member, and inner member, and at least one adjustable end cap assembly.

Referring now to FIGS. 2-3A, the variable stiffness fixation rod 24 as constructed in accordance with one embodiment includes an outer member 110 that can be provided as a sleeve 111, an inner tensioning member 120 such as a cable 121 disposed inside the outer sleeve 111, and an adjustable end cap assembly 70 disposed at one or both terminal ends 33*a-b* of the fixation rod 24. The adjustable end cap assembly 70 thus couples the inner tensioning member 120 to the outer member 110 at least at one end of the fixation rod, and includes a translator that is configured to be actuated to translate one end of the inner tensioning member 120, which correspondingly adjusts the tension and stiffness of the inner tensioning member 120, and thus the overall stiffness of the fixation rod 24. For instance, as the tension of the inner tensioning member 120 is increased, the stiffness of the inner tensioning member 120 is also increased, which increases the overall stiffness of the fixation rod 24. Conversely, as the tension of the inner tensioning member 120 is decreased, the stiffness of the inner tensioning member 120 is also decreased, which decreases the overall stiffness of the fixation rod 24.

The outer member 110 defines a pair of opposing terminal ends 129*a-b* disposed proximate to the terminal ends 33*a-b*, respectively, of the fixation rod 24. The outer member 110 can be provided as an elongated rod-like element, similar to a conventional spinal rod that extends along a longitudinal axis and includes a hollow interior that can be centrally disposed so as to define an internal cannulation 114 extending between the first and second terminal ends 33*a-b*. The outer member 110 can be formed of biocompatible material such as titanium, stainless steel, PEEK or other polymer. In the preferred embodiment, the outer member 110 is capable of bearing a desired amount of load to assist in spinal corrective repair.

The outer member 110 can be provided with an as-manufactured initial or first stiffness or flexibility set by adjusting the amount of material removed during the formation of its cannulation 114. As greater amounts of material are removed to form the cannulation 114, the thickness of the cannulation 114 increases, and the material that defines the outer member 110 decreases in thickness, thereby causing the outer sleeve to have a higher initial flexibility than if the cannulation 114 is formed by removing less material from the outer member 110, thereby causing the cannulation 114 to have a reduced thickness, such that material that defines the outer member 110 has an increased thickness. In this regard, it should be appreciated that the stiffness or flexibility of the fixation rod 24 is defined by a number of components, such as the stiffness or flexibility of the inner member 120, and stiffness or flexibility of the outer member 110 disposed in the cannulation 114. Therefore, as the stiffness of inner member 120 increases and decreases, the overall stiffness of the fixation rod 24 can likewise increase and decrease, respectively. Reference herein to increased or decreased stiffness can be equated to decreased or increased flexibility, respectively, and vice versa.

The inner member 120 is preferably comprised of a flexible or substantially stiff elongated member such as the cable 121 as illustrated, or a tether, or other cord-like member made from titanium, titanium alloys such as titanium-aluminum-niobium alloy (TAN), implant-grade 316L stainless steel, poly-ether-ether-ketone (PEEK) or any suitable alternative implant-grade material. If the inner member 120 is entirely encapsulated by the outer member 110, the inner member 120 may be made from materials other than implant-grade materials, and thus can comprise any suitable plastic or composite. In accordance with one embodiment, the stiffness of the inner member 120 increases as the inner member is put in tension, and decreases as the tension of the inner member 120 is decreased. The inner member 120 defines a pair of opposing terminal ends 123*a-b* disposed proximate to the corresponding terminal ends 129*a-b*, respectively, of the outer member 110, and thus also proximate to the corresponding terminal ends 33*a-b*, respectively, of the fixation rod 24.

Figure 3B:
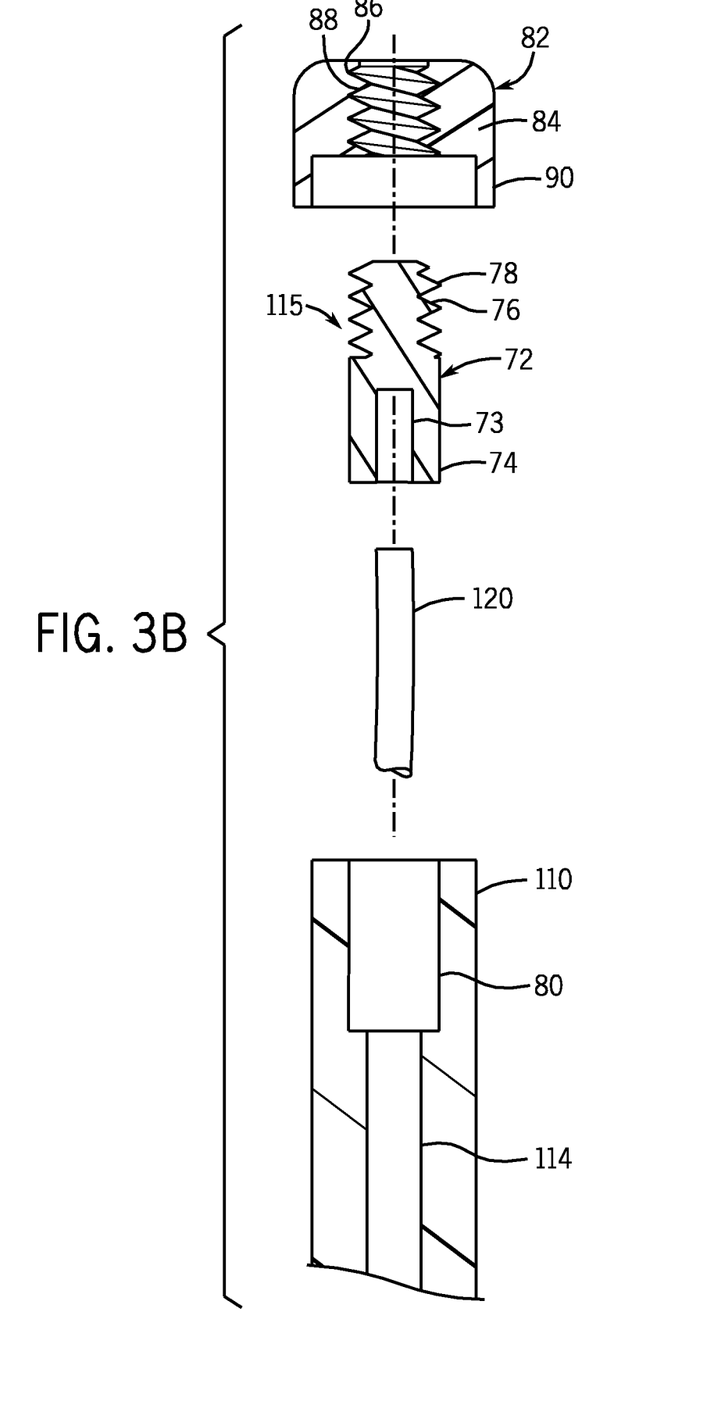
FIG. 3B is an exploded sectional side elevation view of one end of the variable stiffness fixation rod illustrated in FIG. 3A.

Referring now to FIGS. 2-3B, the fixation rod 24 includes an adjustable end cap assembly 70 disposed at each terminal end 33*a* and 33*b*. Each end cap assembly includes an inner generally cylindrical connector 72 that has a longitudinally inner end 74 attached to the longitudinally outer end of the inner tensioning member 120. In the illustrated embodiment, the outer member 110 defines an enlarged cylindrical channel 80 disposed at the opposing outer ends of the cannulation 114 that receives the inner end 74 of the connector 72. The longitudinally inner end 74 of the connector 72 is illustrated as defining a central bore 73 that receives the inner member 120. For instance, the inner member 120 can be adhesively secured in the central bore 73, crimped in the central bore 73, or otherwise secured in the central bore 73 in any desired manner. The connector 72 defines a longitudinally outer end 76 that presents radially outwardly extending threads 78. As will be described in more detail below, the connector 72 translates relative to the outer member 110, and thus provides a translator 115 that causes the corresponding longitudinally outer end of the inner member 120 to translate with the connector 72.

Each end cap assembly 70 further includes an outer cap 82 that defines an annular cap body 84 defining an inner channel 86 having threads 88 protruding therein that are configured to mate with the threads 78 of the connector 72. As shown in FIG. 2, the outer cap body 84 carries an actuator 85 configured to engage any suitable driving tool that can cause the outer cap body 84 to rotate with respect to the inner connector 72. In the illustrated embodiment, the actuator 85 comprises a polygonal radially outer engagement surface 87 configured to be engaged by a wrench, pliers, or even by hand. It should be appreciated that the actuator 85 could define any alternative structure as desired that is capable of being driven in the manner described herein. In accordance with the illustrated embodiment, the actuator 85 rotates to drive the translator 115, though it should be appreciated that the actuator could alternatively translate in the manner described below.

The outer cap 82 further defines a radially outer flange 90 projecting longitudinally inward from the cap body 84. The flange 90 defines an inner diameter substantially equal to, or slightly greater than, the outer diameter of the outer member 110 such that the flange 90 is configured to ride along the outer member 110 during operation. The flange 90 prevents contaminants from entering into the end cap assembly 70 during operation, and provides a guide for the rotation of the outer cap 82. The flange 90 can further engage the outer member 110 in a manner such that the flange 90 is rotatable with respect to the outer member, but is fixed to the outer member 110 with respect to relative longitudinal movement. For instance, an engagement member such as a snap ring 142 (see FIG. 4F) can couple the flange 90, and thus the outer cap 82, to the outer member 110.

Figure 3C:
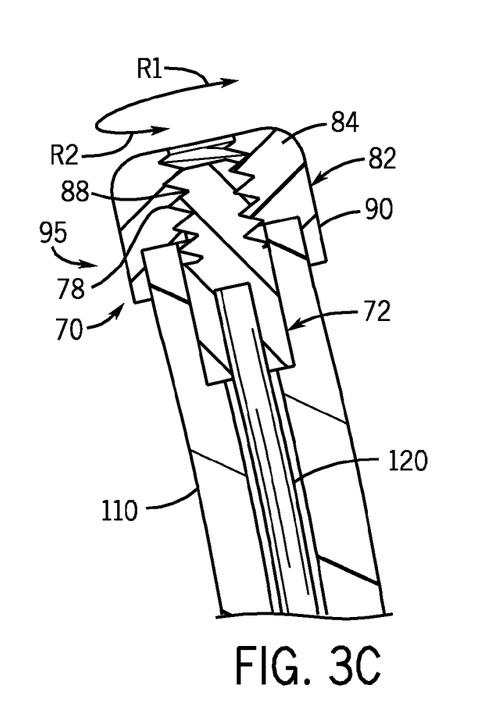
FIG. 3C is a sectional side elevation view of one end of the variable stiffness fixation rod illustrated in FIG. 3A during operation.
Figure 3D:
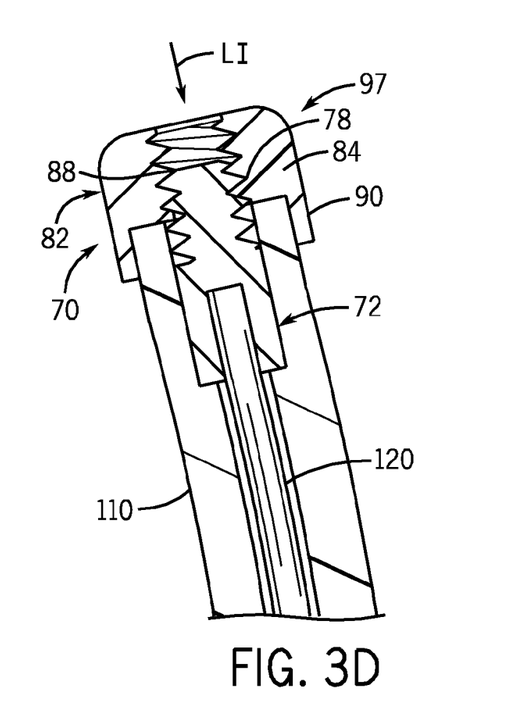
FIG. 3D is another sectional side elevation view of one end of the variable stiffness fixation rod illustrated in FIG. 3A during operation.
Figure 3E:
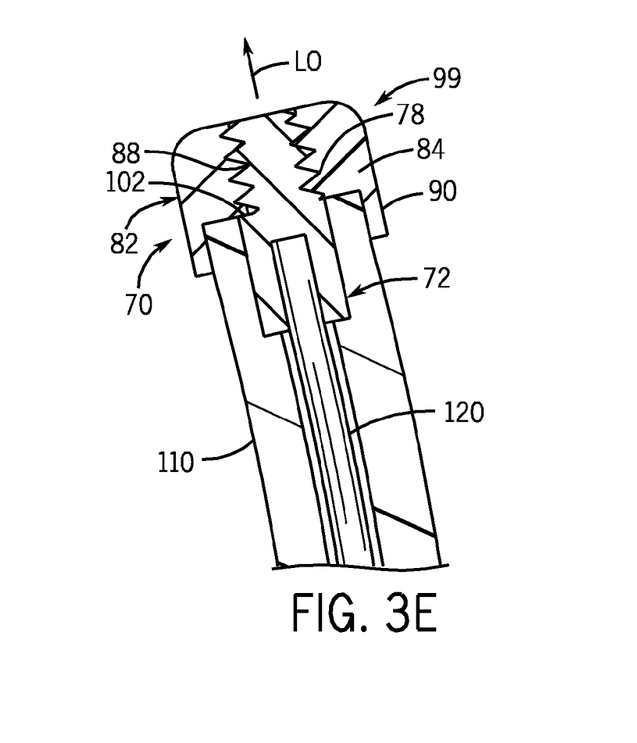
FIG. 3E is a another sectional side elevation view of one end of the variable stiffness fixation rod illustrated in FIG. 3A during operation.

Referring now to FIGS. 3C and 3E, each end cap assembly 70 can be provided in an initial position 95 whereby the inner connector 72 is movable relatively longitudinally outward and relatively inward with respect to the outer cap 82, the inner member 120, and the opposing end cap assembly 70. In particular, the outer cap 82 is movable in a first rotational direction R1 (for instance clockwise) relative to the inner connector 72, which causes the threadedly engaged inner connector 72 to translate relatively longitudinally outward or longitudinally extend with respect to the outer cap 82, the inner member 120, and the opposing end cap assembly 70, in the direction indicated by Arrow LO. As the inner connector 72 moves relatively outward, the tension of the inner member 120 increases to a second stiffness that is greater than the first stiffness, thereby increasing the stiffness of the inner member 120 and thus increasing the overall stiffness of the fixation rod 24. Thus, FIG. 3D illustrates the fixation rod 24 in a position 97 of increased stiffness with respect to the initial stiffness, or prior stiffness, illustrated in FIG. 3C. With continuing reference to FIG. 3E, the inner connector 72 can define a radially outer stop flange 102 that is configured to abut the longitudinally inner end of the outer cap 82 so as to prevent over-rotation of the outer cap 82.

Referring now to FIGS. 3C and 3D, the outer cap the outer cap 82 is movable in a second rotational direction opposite the first rotational direction R2 (for instance counterclockwise) direction relative to the inner connector 72, which causes the threadedly engaged inner connector 72 to translate relatively longitudinally inward or longitudinally retract with respect to the outer cap 82, the inner member 120, and the opposing end cap assembly 70, in the direction indicated by Arrow LI. As the inner connector 72 moves relatively inward, the tension of the inner member 120 decreases to a third stiffness that is less than the first stiffness (or prior stiffness, which could be the second stiffness), thereby decreasing the stiffness of the inner member 120 and thus decreasing the overall stiffness of the fixation rod 24. Thus, FIG. 3D illustrates the fixation rod 24 in a position 99 of decreased stiffness with respect to the initial stiffness, or prior stiffness.

Thus, during operation, the variable stiffness fixation rod 24 is applied between a plurality of (at least two) conventional pedicle screw assemblies of the type illustrated and described above with respect to bone fixation elements 22A-D. The tension of the fixation rod 24 can be adjusted preoperatively or intraoperatively by rotating the outer cap 82 at either or both ends 33a-b of the fixation rod 24 by using a simple instrument by hand.

While the adjustable end cap assembly 70 has been illustrated and described in accordance with one embodiment, it is appreciated that the end cap assembly 70 can be constructed in accordance with numerous alternative embodiments that is configured to selectively extend or retract the inner member 120. Unless otherwise indicated, the end cap assembly 70 is not intended to be limited to any of the embodiments disclosed herein.

Figure 4A:
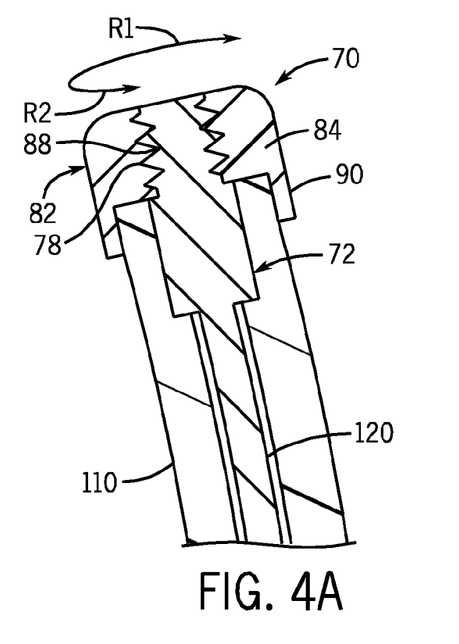
FIG. 4A is a sectional side elevation view of the adjustable end cap assembly illustrated in FIG. 3A, but constructed in accordance with an alternative embodiment.

Referring now to FIG. 4A, the end cap assembly 70 can be configured such that the inner connector 72 is fixedly attached to, or integral with, the inner member 120. Thus, as illustrated, the outer diameter of the inner connector 72, and the corresponding inner diameter of the channel 86 can be greater than the diameter of the inner member 120 as illustrated, or can be substantially equal to or less than the diameter of the inner member 120 if desired.

Figure 4B:
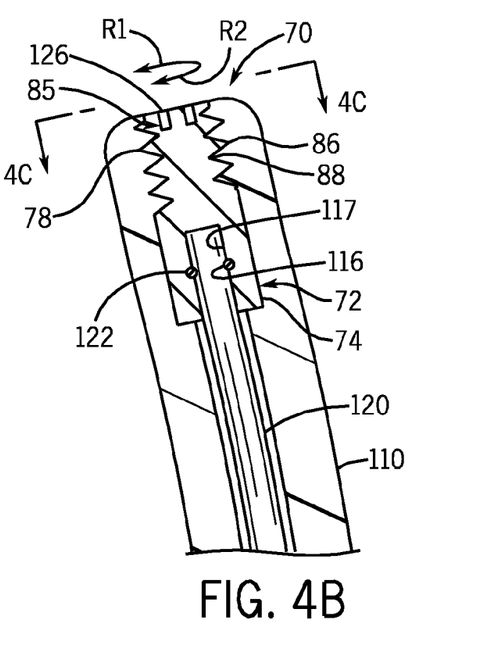
FIG. 4B is a sectional side elevation view of the adjustable end cap assembly illustrated in FIG. 4A, but constructed in accordance with an alternative embodiment.

Referring now to FIG. 4B, it is appreciated that the inner connector 72 can be rotatable with respect to the inner member 120. The inner connector 72 carries a first engagement member in the form of an annular recess 116 projecting radially outward into the surface 117 of the longitudinally inner end 74 of the inner connector 72 that defines the central bore 73. The outer member 110 carries a second engagement member in the form of a protrusion illustrated as an annular snap ring 122 that is fitted over the inner member, and optionally disposed in a recess extending into the inner member, such that the inner member carries the protrusion or snap ring 122. The snap ring 122 is configured to be inserted into the recess 116 and interlock with the recess so as to be rotatable therein, while preventing relative longitudinal movement between the connector 72 and the outer member 110. Accordingly, the inner connector 72 is rotatable with respect to the outer member 110, and the inner member 120 moves longitudinally with the connector 72. It should be appreciated that the first and second engagement members could be alternatively constructed. For instance, the outer member 110 could define a recess and the connector could 72 carry a snap ring or other protrusion as desired.

The longitudinally outer end of the outer member 110 thus defines the inner bore 86 presenting inwardly projecting threads 88 configured to mate with the threads 78 of the connector 72. Thus, as the inner connector 72 is rotated in the first rotational (counterclockwise) direction R1 with respect to the outer member 110, the inner connector 72 translates longitudinally outward with respect to the outer member 110 and the opposing connector 72 of the fixation rod 24, which extends the inner member 120, thereby increasing the tension in the inner member 120, which increases the stiffness of the inner member 120 and also increases the stiffness of the fixation rod 24. As the inner connector 72 is rotated in the second rotational (clockwise) direction R2 with respect to the outer member 110, the inner connector 72 translates longitudinally inward with respect to the outer member 110 and the opposing connector 72 of the fixation rod 24, which retracts the inner member 120, thereby decreasing the tension in the inner member 120, which decreases the stiffness of the inner member 120 and also decreases the stiffness of the fixation rod 24.

Figure 4C:
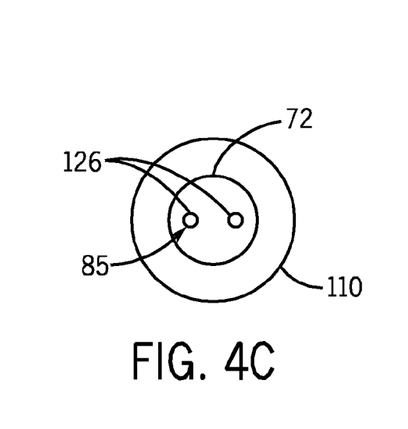
FIG. 4C is an end elevation view of the adjustable end cap assembly illustrated in FIG. 4B, taken along line 4C-4C.

Referring also to FIG. 4C, the inner connector 72 carries the actuator 85 configured to engage any suitable driving tool that can cause the inner connector 72 to rotate with respect to the outer member 110. As illustrated, the actuator 85 includes a pair of apertures 126 extends longitudinally into the longitudinal outer surface of the inner connector 72. The apertures 126 are configured to engage teeth of a driving instrument which can thereby cause the rotation of the inner connector in the directions R1 and R2.

Figure 4D:
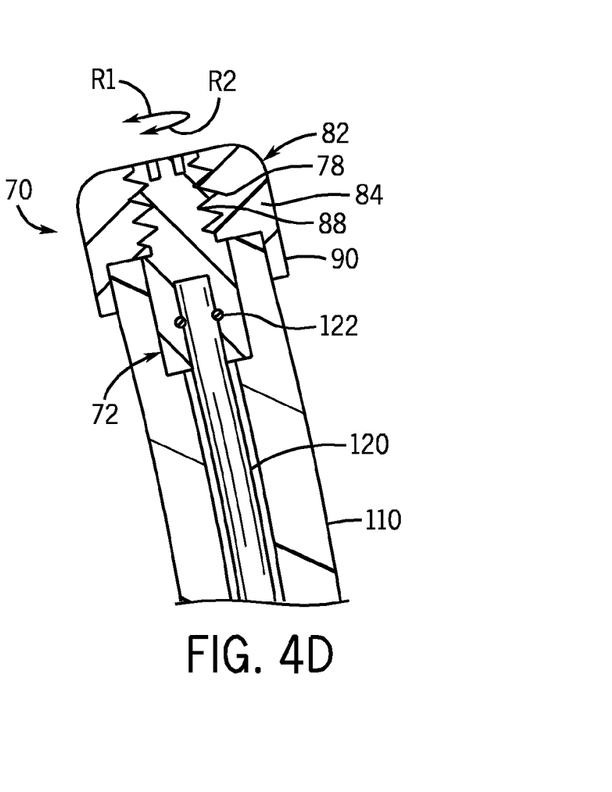
FIG. 4D is a sectional side elevation view of the adjustable end cap assembly illustrated in FIG. 4B, but constructed in accordance with an alternative embodiment.

Referring now to FIG. 4D, the end cap assembly 70 can be constructed substantially as illustrated with respect to FIG. 4C, however, the end cap assembly can include the outer cap 82 of the type illustrated in FIG. 4A. Accordingly, the tension of the inner member 120 can be increased or decreased by rotating either or both of the outer cap 82 and the inner connector 72 relative to each other. Alternatively, the outer cap 82 or the inner connector 72 can be rotatably fixed to the outer member 110. Accordingly, the outer cap 82 or inner connector 72 that is not rotatably fixed to the outer member 110 is configured to rotate relative to the other of the outer cap 82 and inner connector 72, thereby adjusting the tension of the inner member 120 in the manner described above.

Figure 4E:
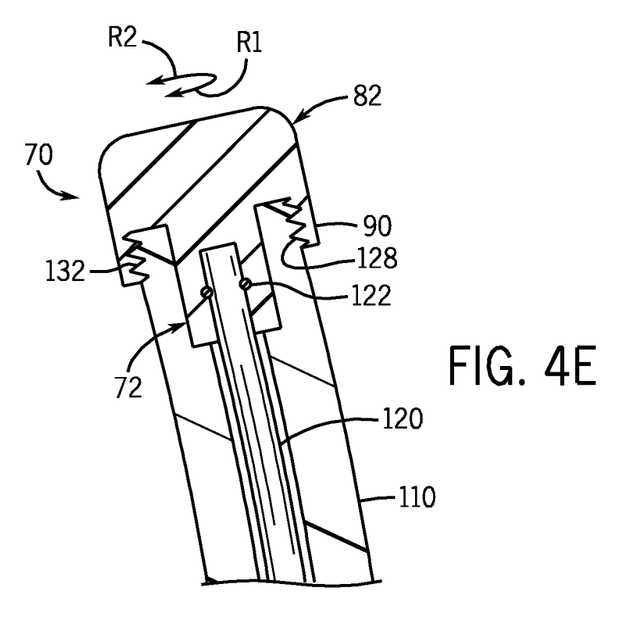
FIG. 4E is a sectional side elevation view of the adjustable end cap assembly illustrated in FIG. 4D, but constructed in accordance with an alternative embodiment.

Referring now to FIG. 4E, the end cap assembly 70 can be constructed substantially as illustrated in FIG. 4D, however the outer cap 82 is fixedly attached to, or integral with, the inner connector 72. The end cap assembly 70 includes threads 128 projecting radially inward from the flange 90, and the longitudinally outer end of the outer member 110 includes threads 132 projecting radially outward therefrom. The threads 128 and 132 are configured to engage such that rotation of the outer cap 82 relative to the outer member 110 in the first (clockwise) rotational direction R1 causes the end cap assembly 70 to translate longitudinally outward relative to the outer member 110 and the opposing end cap assembly 70, thereby extending the inner member 120 and increasing the tension and stiffness of the inner member 120, which increases the stiffness of the fixation rod 24. Rotation of the outer cap 82 relative to the outer member 110 in the second (clockwise) rotational direction R2 causes the end cap assembly 70 to translate longitudinally outward relative to the outer member 110 and the opposing end cap assembly 70, thereby retracting the inner member 120 and decreasing the tension and stiffness of the inner member 120, which decreases the stiffness of the fixation rod 24.

Figure 4F:
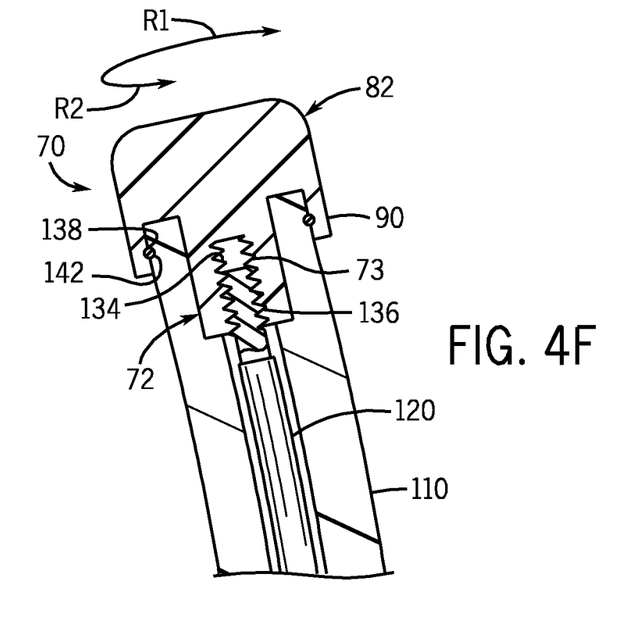
FIG. 4F is a sectional side elevation view of the adjustable end cap assembly illustrated in FIG. 4E, but constructed in accordance with an alternative embodiment.

Referring now to FIG. 4F, the end cap assembly can be constructed such that the outer cap 82 is fixedly attached to, or integral with, the inner connector 72 as illustrated in FIG. 4E. However, the inner connector 72 and the inner member 120 do not include interlocking first and second engagement members. Furthermore, the outer cap 82 is not threadedly connected to the outer member 110. Rather, the central bore 73 of the connector 72 carries radially inwardly projecting threads 134, and the longitudinally outer end of the inner member 120 carries radially outwardly projecting threads 136 that mate with the threads 134.

The outer cap 82 carries a first engagement member in the form of an annular recess 138 projecting radially outward into the radially inner surface of the flange 90. The outer member 110 carries a second engagement member in the form of a protrusion illustrated as an annular snap ring 142 that is fitted over the outer member 110, and optionally inserted into a recess extending into the outer member 110, such that the outer member 110 carries the protrusion or snap ring 142. The snap ring 122 is configured to be inserted into the recess 138 and interlock with the recess 138 so as to be rotatable therein, while preventing relative longitudinal movement between the outer cap 82, and thus the connector 72, and the outer member 110. Accordingly, the inner connector 72 and outer cap 82 are rotatable with respect to the outer member 110, and the inner connector 72 and the outer cap 82 are fixed with the outer member 110 with respect to relative longitudinal movement.

During operation, as the end cap assembly 70 is rotated in the first (clockwise) direction R1, the inner connector 72 rotates relative to the inner member 120, which causes the inner member 120 to extend longitudinally inward within the bore 73, thereby increasing the tension and stiffness of the inner member 120, and increasing the stiffness of the fixation rod 24. As the end cap assembly 70 is rotated in the second (counterclockwise) direction R2, the inner connector 72 rotates relative to the inner member 120, which causes the inner member to retract longitudinally inwardly within the bore 73, thereby decreasing the tension and stiffness of the inner member 120, and decreasing the stiffness of the fixation rod 24.

Figure 4G:
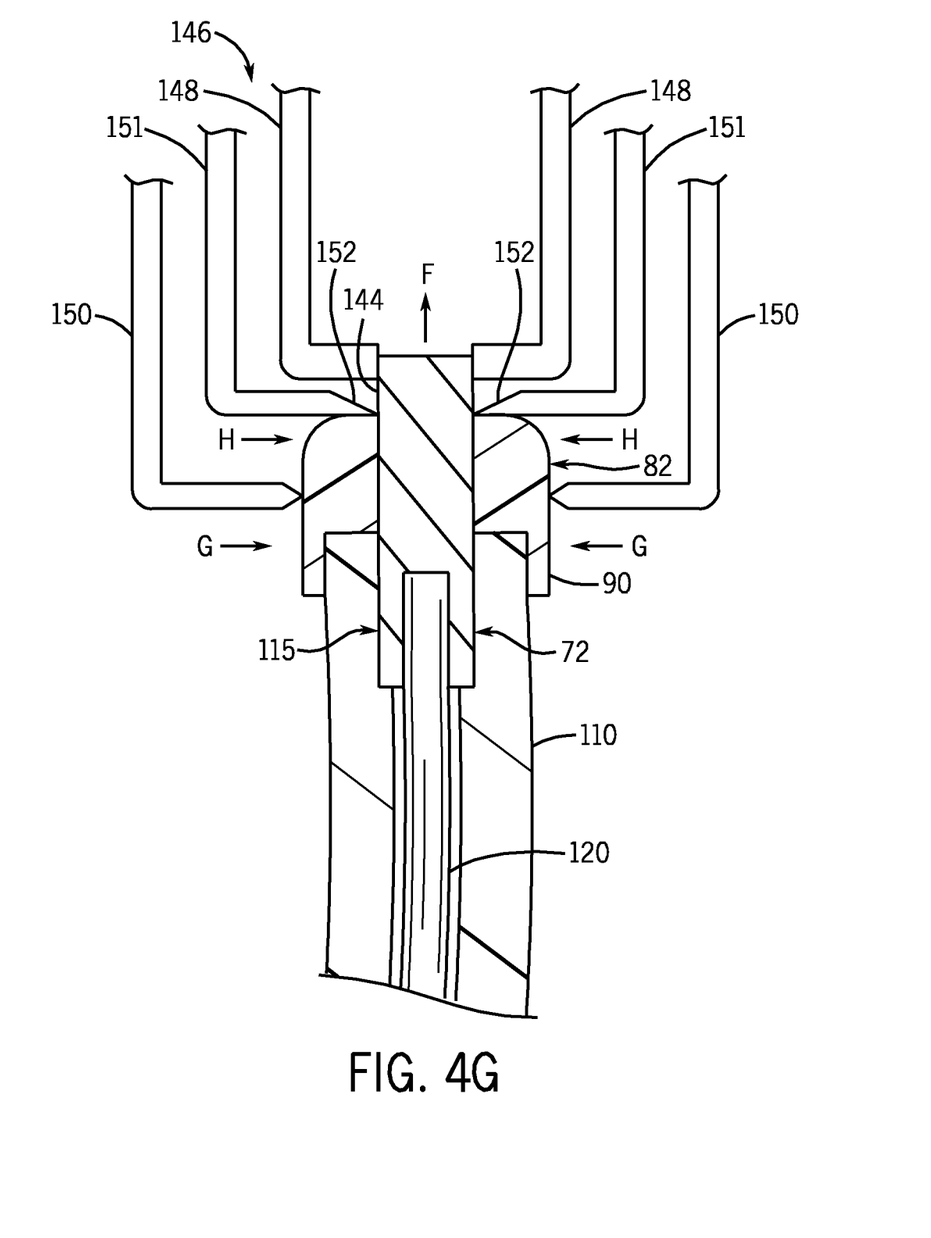
FIG. 4G is a sectional side elevation view of the adjustable end cap assembly illustrated in FIG. 4F, but constructed in accordance with an alternative embodiment.

Referring now to FIG. 4G, it is further appreciated that the end cap assembly 70 can be provided in accordance with an alternative embodiment, whereby the inner member 120 is translated or extended longitudinally outward with respect to the outer member 110 and the opposing end cap assembly without inducing rotation in the end cap assembly. For instance, the inner connector 72 can be attached to the inner member 120 in any manner described above, and the inner connector can define a longitudinally outer portion 144 that protrudes longitudinally out from the outer cap 82, and thereby provides an actuator that is configured to translate, thereby driving the translator 115, which is provided by the connector 72.

Any suitable crimping mechanism 146 can be provided having a first pair of arms 148 that are configured to engage and retain the longitudinally outer end 144 of the connector 72, and translate the connector 72 longitudinally outward in the first direction of Arrow F, thereby extending the inner member 120 and increasing the tension and stiffness of the inner member, which increases the stiffness of the fixation rod 24. Next, a pair of crimp arms 150 can engage the radially outer surface of the outer cap 82 along the direction of Arrow G, thereby crimping the outer cap 82 against the connector 72 so as to lock the connector 72 and inner member 120 in their longitudinally extended position. Finally, a pair of cutter blades 152 carried by corresponding cutter arms 151 can cut, in the direction of Arrow H, the excess portion of the connector 72 that extends longitudinally beyond the outer cap 82.

It should be appreciated that the outer cap 82, or alternatively the outer member 110 of the adjustable end cap assembly 70 constructed in accordance with any of the embodiments described herein, can be crimped in accordance with any of the embodiments described above if it is desired to provide the fixation rod 24 with a preset stiffness during manufacturing and assembly. In this regard, it should be appreciated that a kit can be provided that includes a plurality of variable stiffness fixation rods 24 throughout a range of preset stiffnesses.

Figure 5:
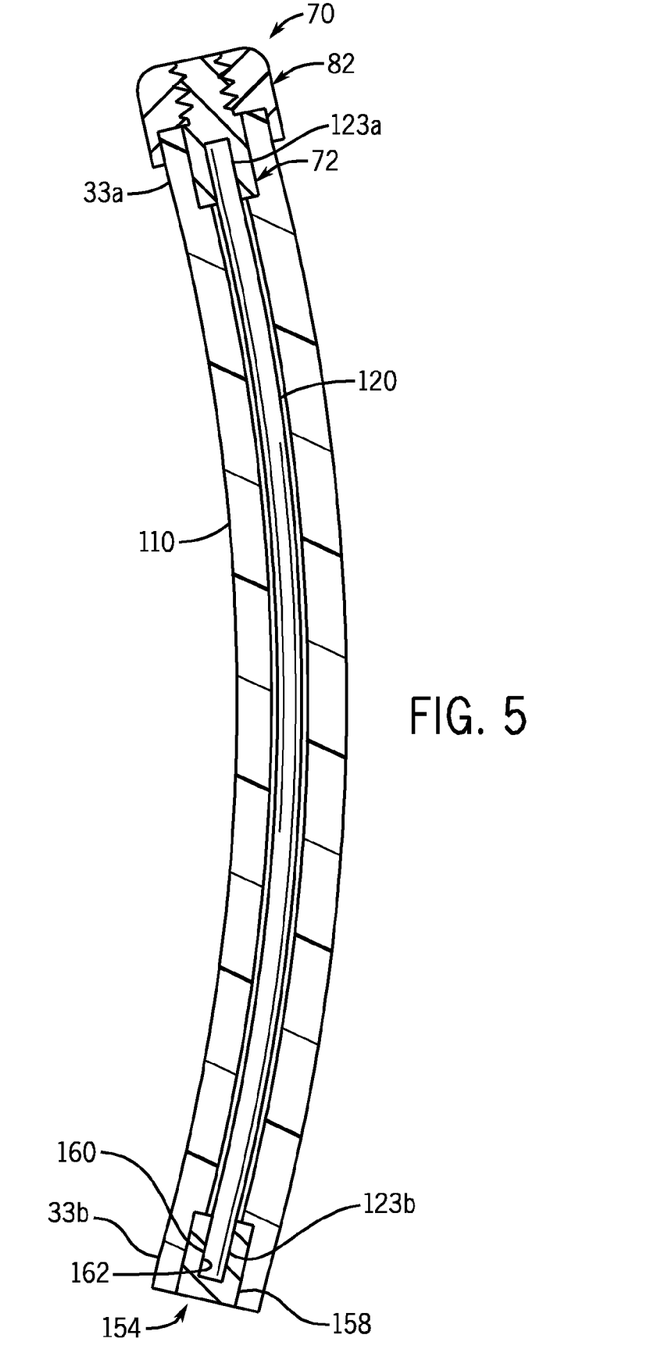
FIG. 5 is a sectional side elevation view of the variable stiffness fixation rod illustrated in FIG. 3A, but including a fixed end cap assembly in accordance with another embodiment.

Referring now to FIG. 5, it is appreciated that while the fixation rod 24 has been illustrated and described herein as including an adjustable end cap assembly 70 at both terminal ends 33a-b, it is appreciated that the adjustable end cap assembly 70 can be provided at only one of the ends 33a-b, while the other of the ends 33a-b can include a fixed end cap assembly 154 that is not configured to adjust the tension of the inner member 120. The fixed end cap assembly 154 can be provided as any suitable structure that fixes the inner member 120 with respect to the outer member 110 at or proximate to one of the ends 33a-b (33b as illustrated), or anywhere along the length of the outer member 110. In accordance with the illustrated embodiment, the fixed end cap assembly 154 includes a fixed connector 156 that is attached to, or integral with, the outer member 110. The connector 156 includes a connector body 158 that defines a bore 160 extending into the longitudinally inner surface 162 of the connector body 158 in a longitudinally outward direction. The bore 160 is configured to receive, and attach to, the inner member 120. The connector body 158 can alternatively be integral with the inner member 120. Furthermore, one or both of the outer member 110 and the connector 156 can be crimped against the end 123b of the inner member 120. Accordingly, actuation of the opposing adjustable end cap assembly causes longitudinal movement of the opposing end 123a of the inner member 120 relative to the fixed end cap assembly 154 as opposed to an opposing adjustable end cap assembly as described above.

The variable stiffness rod 24 can be applied between any conventional polyaxial or monoaxial pedicle screws and preferably does not require additional elements common to prior art dynamic stabilization devices such as bumpers or other spacing members, shielding elements for protecting the interaction between polymer and metallic elements, special locking caps and/or pedicle screw assemblies, or flared rod portions.

The adjustable end cap assemblies 70 at either or both of the ends 33a-b of the fixation rod 24 can be constructed in accordance with any of the embodiments illustrated and described above. In this regard, it should be appreciated that the terminal ends 33a-b can include adjustable end cap assemblies of the same embodiments, or of different embodiments. Thus, the end cap assembly 70 disposed at the end 33a of the fixation rod 24 can be constructed the same or differently than the end cap assembly 70 disposed at the end 33b of the fixation rod 24. In this regard, it should be appreciated that the kit can include fixation rods 24 having different adjustable end cap assemblies 70 of the type described herein disposed at one or both of the terminal ends 33a-b. The one or more of the fixation rods 24 can further include the fixed end cap assembly 154 in the manner described above.

Figure 6A:
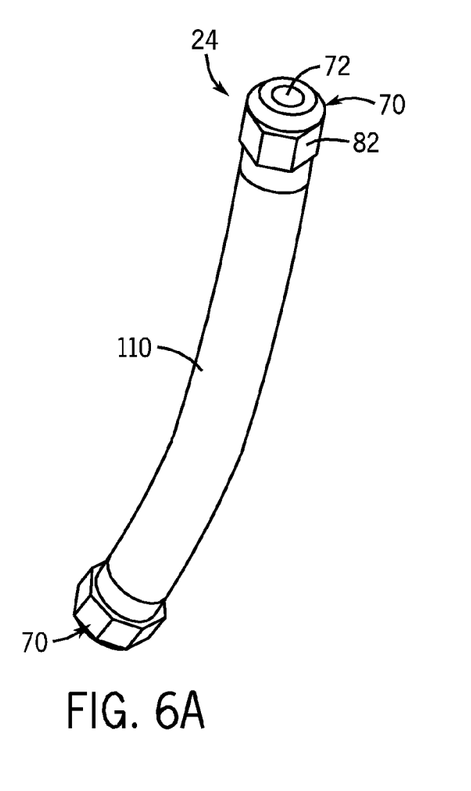
FIGS. 6A-C are perspective views of variable stiffness fixation rods having different curved profiles.
Figure 6B:
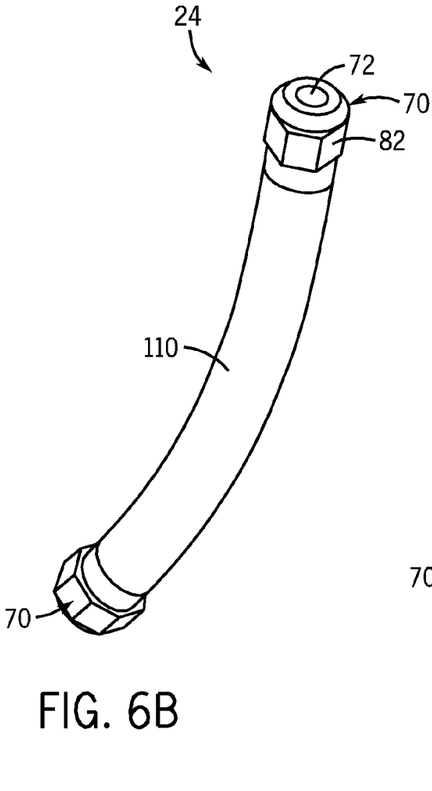
Figure 6C:
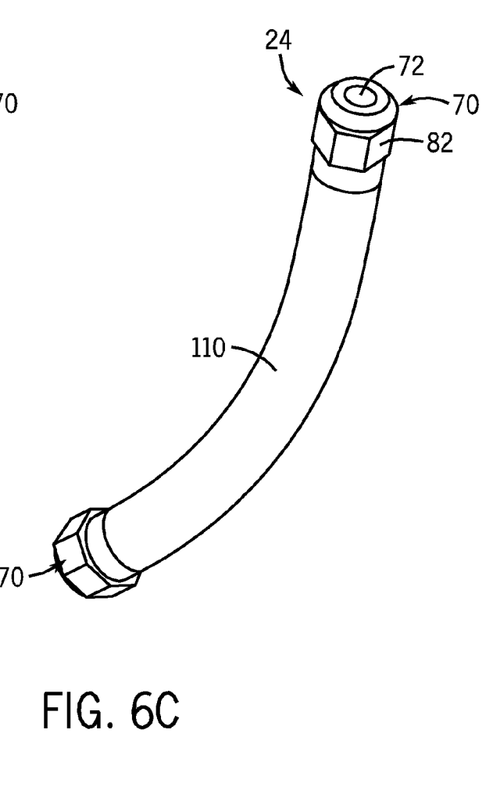

Referring now to FIGS. 6A-C, it is appreciated that the kit can further include a plurality of fixation rods 24 that define varying curvature profiles. For instance, the fixation rod 24 illustrated in FIG. 6A defines a first curvature, the fixation rod illustrated in FIG. 6B defines a second curvature greater than the first curvature, and the fixation rod illustrated in FIG. 6C defines a third curvature greater than the second curvature. One or more, up to all, of the fixation rods 24 illustrated in FIGS. 6A-C can include the adjustable end cap assembly 70 constructed in accordance with any of the embodiments illustrated and described herein at one or both ends 33a-b, and can further include the fixed end cap assembly 154 at one of the ends 33a-b in the manner described above.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the present description.

What is claimed is:

1. A variable stiffness rod configured to span between two or more adjacent vertebral fixation elements, each vertebral fixation element including a channel formed therein configured to receive the variable stiffness rod, the variable stiffness rod elongate along a longitudinal direction, the variable stiffness rod comprising:
   an outer member being an elongated rod-like element having a first end and an opposing second end, the outer member configured to extend through the respective channels of each of the two or more adjacent vertebral fixation elements, the outer member defining an interior cannulation extending between the first and second ends;
   an inner tensioning member configured to be disposed in the cannulation of the outer member, the inner tensioning member having a first stiffness; and
   an adjustable end cap assembly disposed at least at one of the first and second ends, the adjustable end cap assembly configured to couple the inner tensioning member to the outer member, the adjustable end cap assembly including a translator coupled to the inner tensioning member, wherein a portion of the inner tensioning member is disposed within the translator, the translator configured to move from a first position to a second position relative to the outer member along the longitudinal direction, and an actuator configured to move in a first direction to drive the translator from the first position to the second position, wherein when the translator is in the second position, the inner tensioning member is in an extended state and achieves a second stiffness that is greater than the first stiffness.

2. The variable stiffness rod as recited in claim 1, wherein the actuator is configured move in a second direction that drives the translator from the second position to a third position so as to retract the inner tensioning member, such that the inner tensioning member achieves a third stiffness that is less than the first stiffness.

3. The variable stiffness rod as recited in claim 2, wherein the adjustable end cap assembly comprises an outer cap that carries the actuator, and the translator is configured as an inner connector that couples the inner tensioning member to the outer cap.

4. The variable stiffness rod as recited in claim 3, wherein the outer cap is threadedly connected to the inner connector, such that rotation of the outer cap relative to the inner connector in the first direction causes the inner connector and the coupled inner tensioning member to translate outward.

5. The variable stiffness rod as recited in claim 4, wherein rotation of the outer cap relative to the inner connector in the second direction causes the inner connector and the coupled inner tensioning member to translate inward.

6. The variable stiffness rod as recited in claim 3, wherein the outer cap is threadedly connected to the outer member and fixedly attached to the connector, such that rotation of the end cap relative to the outer member causes the connector to translate the inner tensioning member.

7. The variable stiffness rod as recited in claim 6, wherein the end cap is integrally connected to the connector.

8. The variable stiffness rod as recited in claim 1, wherein the adjustable end cap assembly comprises a connector that carries the actuator, and the connector is further coupled to the inner tensioning member such that the connector provides the translator.

9. The variable stiffness rod as recited in claim 8, wherein the connector is threadedly coupled to the outer member, such that rotation of the connector relative to the outer member in the first direction causes the inner connector and the coupled inner tensioning member to translate outward.

10. The variable stiffness rod as recited in claim 9, wherein rotation of the connector relative to the outer member in a second direction causes the connector and the coupled inner tensioning member to translate inward.

11. The variable stiffness rod as recited in claim 8, wherein the adjustable end cap assembly further comprises an outer cap that fits over the outer member, and the connector is threadedly connected to the outer cap.

12. The variable stiffness rod as recited in claim 8, wherein the connector is translatable relative to the outer member, thereby causing the inner tensioning member to translate relative to the outer member.

13. The variable stiffness rod as recited in claim 12, wherein the connector comprises an outer portion that protrudes past the outer member, and the outer portion is configured to be engaged and pulled outward.

14. The variable stiffness rod as recited in claim 13, wherein the adjustable end cap assembly further comprises an outer cap coupled to the outer member, the end cap further receiving the connector such that the outer portion protrudes past the outer cap.

15. The variable stiffness rod as recited in claim 1, wherein the rod defines a curvature.

16. The variable stiffness rod as recited in claim 1, further comprising a second end cap assembly disposed at the other of the first and second ends, the second end cap assembly configured to couple the inner tensioning member and the outer member.

17. The variable stiffness rod as recited in claim 16, wherein the second end cap assembly is adjustable so as to vary the stiffness of the inner tensioning member.

18. The variable stiffness rod as recited in claim 16, wherein the second end cap assembly is not configured to adjust the stiffness of the inner tensioning member.

19. A kit comprising a plurality of variable stiffness rods, each variable stiffness rod configured to span between two or more adjacent vertebral fixation elements, each vertebral fixation element including a channel formed therein configured to receive the variable stiffness rod, each variable stiffness rod elongate along a longitudinal direction, each variable stiffness rod comprising:

an outer member being an elongated rod-like element having a first end and an opposing second end, the outer member configured to extend through the respective channels of each of the two or more adjacent vertebral fixation elements, the outer member defining an interior cannulation extending between the first and second ends;

an inner tensioning member configured to be disposed in the cannulation of the outer member, the inner tensioning member having a first stiffness; and an adjustable end cap assembly disposed at least at one of the first and second ends, the adjustable end cap assembly configured to couple the inner tensioning member to the outer member, the adjustable end cap assembly including a translator coupled to the inner tensioning member, and an actuator configured to move the translator from a first position into a second position, wherein when the translator is in the second position, the inner tensioning member is in an extended state and achieves a second stiffness that is greater than the first stiffness, wherein at least one of the variable stiffness rods has a different curvature with respect to one of the other variable stiffness rods, and the translator surrounds at least a portion of the inner tensioning member.

20. The kit as recited in claim 19, wherein the adjustable end cap assembly comprises an outer cap that carries the actuator, and the translator is configured as an inner connector that couples the inner tensioning member to the outer cap.

21. The variable stiffness rod as recited in claim 19, wherein the adjustable end cap assembly comprises a connector that carries the actuator, and the connector is further coupled to the inner tensioning member such that the connector provides the translator.

\* \* \* \* \*